United States Patent [19]

Kakimoto et al.

[11] Patent Number: 4,919,917
[45] Date of Patent: Apr. 24, 1990

[54] AGENT FOR REDUCING NEPHROTOXICITY CAUSED BY CYCLOSPORIN ADMINISTRATION

[75] Inventors: Norihiro Kakimoto, Machida; Kazuo Kumano, Yamato; Kunie Nakamura, Sagamihara, all of Japan

[73] Assignee: Asai Germanium Research Institute Co., Ltd., Tokyo, Japan

[21] Appl. No.: 261,406

[22] Filed: Oct. 24, 1988

[30] Foreign Application Priority Data

Oct. 29, 1987 [JP] Japan ................................. 62-273746

[51] Int. Cl.$^5$ .............................................. A61K 31/28
[52] U.S. Cl. ...................................... 424/10; 514/492
[58] Field of Search ....................... 424/10; 514/492, 2, 514/11, 885

[56] References Cited

FOREIGN PATENT DOCUMENTS 0016444 10/1980 European Pat. Off. .
1257225 12/1971 United Kingdom .
1365997 9/1974 United Kingdom .
2142635 1/1985 United Kingdom .
2143128 2/1985 United Kingdom .
2191697 12/1987 United Kingdom .

OTHER PUBLICATIONS

Chem. Abstracts 107(1):471g "Mechanisms of Cyclosporin A Hypertension", Lustig et al., 7/6/87.

Primary Examiner—Douglas W. Robinson
Assistant Examiner—Raymond J. Henley III
Attorney, Agent, or Firm—Burns, Doane, Swecker & Mathis

[57] ABSTRACT

The present invention provides (1) an agent for reducing the nephrotoxicity caused by cyclosporin administration, characterized by containing, as an effective component, an organogermanium compound represented by the formula (I)

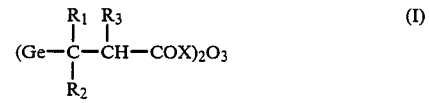

wherein $R_1$ to $R_3$ are each a hydrogen atom, a lower alkyl group such as methyl, ethyl or the like which may be the same or different, or a substituted or unsubstituted phenyl group, and X is a hydroxyl group, an O-lower alkyl group, an amino group or $O^-Y^+$ (Y is a metal such as sodium, potassium or the like, or a basic group-containing compound such as lysozyme, basic amino acid or the like), and (2) a method for reducing the nephrotoxicity caused by cyclosporin administration, characterized by administering, in need of such treatment, an effective amount of an organogermanium compound represented by the above formula (I).

6 Claims, 2 Drawing Sheets

A: Present agent-administered group
B: Ciclosporin-administered group

A: Present agent-administered group
B: Ciclosporin-administered group

AGENT FOR REDUCING NEPHROTOXICITY CAUSED BY CYCLOSPORIN ADMINISTRATION

BACKGROUND OF THE INVENTION

1. Field of the Invention

The present invention relates to an agent for reducing the nephrotoxicity appearing in living bodies to which cyclosporin has been administered. More particularly, the present invention relates to an agent for reducing the nephrotoxicity caused by cyclosporin administration, which contains a particular organogermanium compound as an effective component.

2. Description of the Prior Art

Cyclosporin, which is a compound extracted from fungi in the soil, effectively suppresses a so-called rejection reaction which is the biggest problem in organ transplants, i.e., an immune reaction between transplanted organ and host and, as a further advantage, does not weaken the power of resistance of transplanted organs against viruses. Accordingly, cyclosporin is highly evaluated as a drug which has remarkably enhanced the possibility of organ transplant operations.

The immunosuppression effect of cyclosporin is striking. It is reported that the graft survival rate after one year when kidney transplant has been conducted using cyclosporin is about 80% when using cadaveric kidneys and about 93% when using living kidneys, showing a significant improvement over the control using no cyclosporin.

The biggest clinical problem in using cyclosporin, however, is its strong toxicity to the kidney. As an example, there is reported a case in which organ transplant was successfully conducted but the cyclosporin administered to suppress the rejection reaction reduced the functions of the transplanted kidney making it necessary to adopt artificial dialysis.

The nephrotoxicity caused by cyclosporin administration can be classified into acute toxicity and chronic toxicity. These toxicities appear in the form of reduced kidney function such as an increase in serum creatinine, decrease in creatinine clearance and the like. In the case of acute toxicity, kidney function can be restored by the stopping of cyclosporin administration. In the case of chronic toxicity, it is thought that chronic toxicity does not progress further when the cyclosporin administration is stopped, although the stopping does not improve the reduced kidney function. In any event, the cyclosporin administration must be stopped in some cases in order to avoid nephrotoxicity, however, this stoppage results in the restoration of immunological competence and the resultant appearance of a rejection reaction, which incurs the functional loss of the transplanted organ in some cases.

SUMMARY OF THE INVENTION

In view of the foregoing prior art, the present invention has been made in order to provide a drug capable of reducing the strong nephrotoxicity of cyclosporin without impairing its immunosuppression effect.

In considering that cyclosporin is administered under conditions such that the organ to be transplanted has a low resistance both before and after the transplant operation, another object of the present invention is to provide an agent for reducing the nephrotoxicity of cyclosporin, which agent has no toxicity and no side effects.

The constitution adopted by the present invention in order to achieve the above objects lies in an agent for reducing the nephrotoxicity caused by cyclosporin administration, characterized by containing, as as an effective component, an organogermanium compound represented by the formula (I)

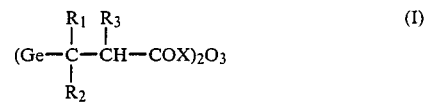

wherein $R_1$ to $R_3$ are each a hydrogen atom, a lower alkyl group such as methyl, ethyl or the like which may be the same or different, or a substituted or unsubstituted phenyl group, and X is a hydroxyl group, an O-lower alkyl group, an amino group or $O^-Y^+$ (Y is a metal such as sodium, potassium or the like, or a basic group-containing compound such as lysozyme, basic amino acid or the like).

DETAILED DESCRIPTION OF THE PREFERRED EMBODIMENTS

Figure 1B:
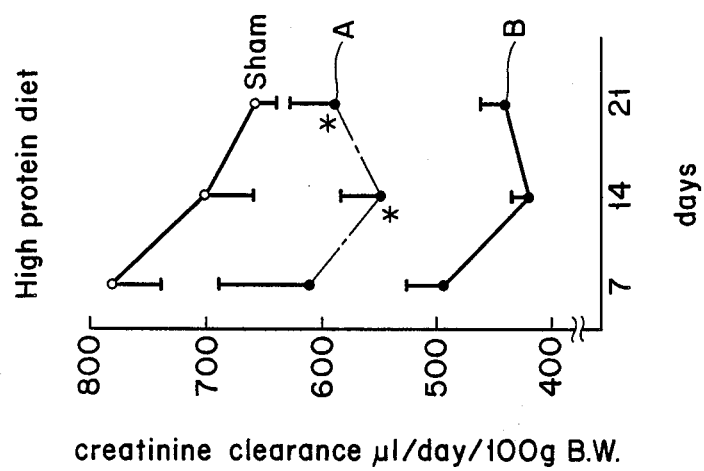
FIG. 1a and FIG. 1b are graphs showing that reduction in creatinine clearance can be improved by the agent of the present invention.

The nephrotoxicity-reducing agent according to the present invention contains, as an effective component, a particular organogermanium compound represented by the formula (I). Hence, this compound is explained first. The compound has, as its basic skeleton, a germylpropionic acid formed by the bonding of a germanium atom and a propionic acid derivative having three substituents $R_1$ to $R_3$ and an oxygen functional group OX, in which basic skeleton of the germanium atom and the oxygen atom is 2:3.

The substituents $R_1$ to $R_3$ are each a hydrogen atom, a lower alkyl group such as methyl, ethyl, propyl, butyl or the like, or a substituted or unsubstituted phenyl group; the substituent X is a hydroxyl group, an O-lower alkyl group, an amino group or a salt of carboxylic acid represented by $O^-Y^+$.

Y is a metal such as sodium, potassium or the like (the metal is not restricted to a monovalent metal), or a basic group containing a compound such as lysozyme, basic amino acid such as lysine or the like.

The substituents $R_1$ and $R_2$ bond to the a-position of the germanium atom and the substituent $R_3$ bonds to the b-position of the germanium atom. Accordingly, specific examples of the organogermanium compound used in the nephrotoxicity-reducing agent according to the present invention are as follows.

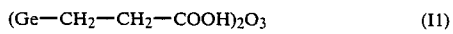

(II)

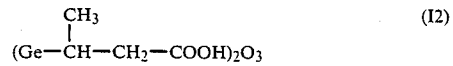

(I2)

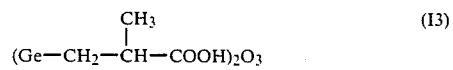

(I3)

-continued

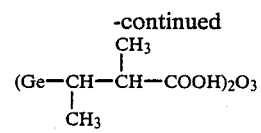 (I4)

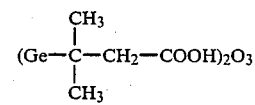 (I5)

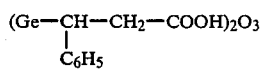 (I6)

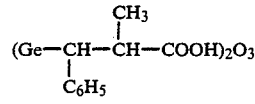 (I7)

$(Ge-CH_2-CH_2-COOCH_3)_2O_3$ (I8)
$(Ge-CH_2-CH_2-CONH_2)_2O_3$ (I9)
$(Ge-CH_2-CH_2-COO^-Na^+)_2O_3$ (I10)

The organogermanium compounds having the above structures can be produced according to various methods.

Those compounds of the formula (I) wherein X=OH can be produced, for example, by hydrolyzing a trihalogermylpropionic acid already having three substituents $R_1$ to $R_3$, such as trichlorogermylpropionic acid (1), as shown in the following reaction formula.

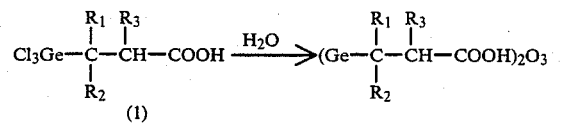

Those compounds of the formula (I) wherein X is a lower alkyl group can be produced, for example, by reacting the above compound (I) with thionyl chloride or the like to convert the former to a corresponding acid halide, reacting the acid halide with an alcohol corresponding to the lower alkyl group, and then hydrolyzing the reaction product. Those compounds of the formula (I) wherein $X=NH_2$ can be produced, for example, by reacting the above acid halide with $NH_3$ and then hydrolyzing the reaction product. Those compounds of the formula (I) wherein $X=O^-Y^+$ and $Y=a$ metal can be produced by reacting the above compound (1) with a corresponding metal hydroxide. Those compounds of the formula (I) wherein $X=O^-Y^+$ and $Y=a$ basic group-containing compound can be produced according to an ordinary acid-base reaction.

The analytical result obtained for the thus produced organogermanium compounds using instrumental analysis methods such as NMR spectroscopy, infrared spectroscopy and the like well support that they are compounds represented by the general formula (I).

The nephrotoxicity-reducing agent of the present invention containing, as an effective component, a particular organogermanium compound obtained by the above synthesis can be administered orally or parenterally. It can be administered in the same form as cyclosporin. That is, when administered orally, it can take a form of tablet, powder, granule or the like and, when administered parenterally, it can take a form of injection. At the stage when cyclosporin administration is switched to oral administration, the present agent also is switched to oral administration.

The organogermanium compound which is an effective component in the present agent is characterized by having very low toxicity and substantially no side effects and accordingly can be administered in a wide range of doses, for example, 20–200 mg/Kg/day.

The present agent can substantially reduce the nephrotoxicity of cyclosporin (which is said to be the biggest drawback of cyclosporin), by using the present agent in combination with cyclosporin. In experiments with mice, the diseases caused by the nephrotoxicity of cyclosporin were effectively improved by the use of the present agent.

The effects of the present agent are shown below by way of Example.

Since the nephrotoxcity of cyclosporin had been studied by model experiments using various animal, the efficacy of the present agent was also confirmed by a model experiment as shown below.

(1) Experimental method

Male SD rats each weighing 280–320 g were subjected to anesthesia by Nembutal ®, a trademark for pentobarbital sodium by Abbott Laboratories. Then their right kidney was enucleated. From two days later, cyclosporin was continuously administered for 21 days in an amount of 15 mg/Kg/day. Part of the rats were fed with high protein (36%) diet in order to increase nephrotoxicity.

As the present agent, there was used the organogermanium compound of the formula (I-1), and 50 mg of the compound was administered peritoneally.

A sham control group was also tested. The numbers of experimental groups and rats were as follows.

|  | Untreated | | Present agent administered | |
| --- | --- | --- | --- | --- |
|  | Normal protein | High protein | Normal protein | High protein |
| Sham control group | 6 | 6 | 6 | 6 |
| Cyclosporin-administered group | 8 | 8 | 8 | 8 |

Each rat was placed in a metabolism cage in the 7th day, 14th day and 21st day from the cyclosporin administration, and their urine was collected for 24 hours and measurements were made of their body weight and the amount of diet consumed by each rat.

The next day, blood was collected under light etherization and a blood test and urine test were conducted. On the 21st day, all the rats were sacrificed and the weight of the left kidney of each rat was measured.

(2) Results (a) Improvement of reduction in creatinine clearance

As compared with the sham control group, the cyclosporin-administered group had a reduced creatinine clearance of 25–35% and, when fed with a high protein diet, it was about 40–45%.

Figure 1A:
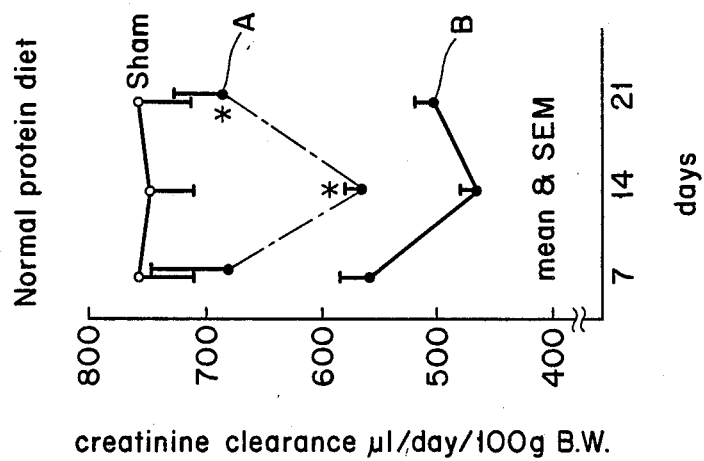

The present agent-administered group, when fed with a normal protein diet and also when fed with a high protein diet, significantly improved the creatinine clearance reduction caused by a cyclosporin, as seen in FIG. 1a and FIG. 1b. (In FIG. 1a and FIG. 1b, * indicates $P<0.05$.)

Incidentally, creatinine clearance is believed to be a meaningful yardstick for the clinical or experimental evaluation of kidney function. It is used particularly in small animals because their serum creatinine values are sometimes near the lower limit of the measurement sensitivity. Further, creatinine clearance is not troublesome to measure as compared with inulin clearance.

(b) Improvement of reduction in kidney weight

All the rats fed with a high protein diet showed larger kidney weights than the respective groups fed with a normal protein diet, due possibly to compensatory hypertrophy.

Figure 2B:
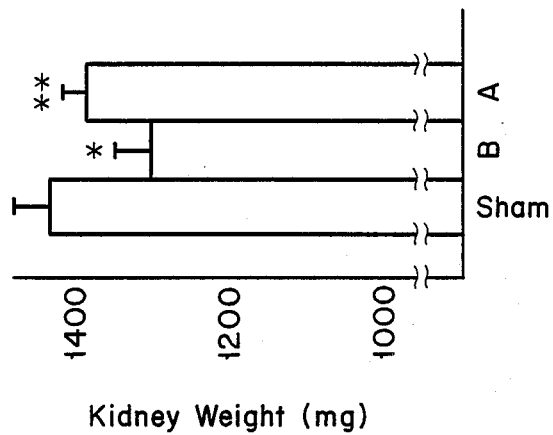
FIG. 2 is a graph showing that reduction in kidney weight can be improved by the agent of the present invention.
Figure 2A:
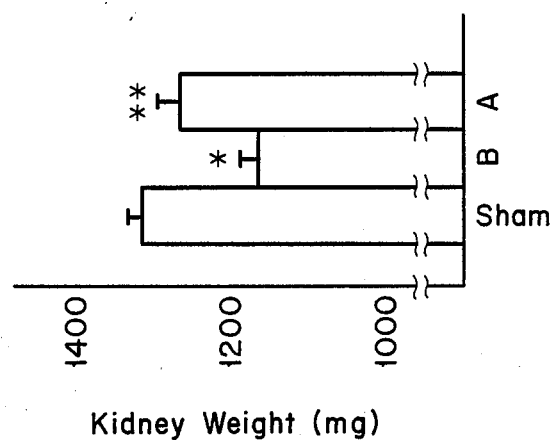

The kidney weights of the cyclosporin-administered group were significantly lower than those of the sham control group. The reduction in kidney weight in the cyclosporin-administered group showed a significant improvement when the present agent was administered in combination with cyclosporin. These results are shown in in FIG. 2. (In FIG. 2., * indicates $P<0.05$ and ** indicates $P<0.5$.)

Similar result were also obtained when other organogermanium compounds represented by the formula (I) were used.

As is appreciated from the above description, the present agent is excellent as an agent for reducing the nephrotoxicity caused by cyclosporin administration.

What is claimed is:

1. A method for reducing the nephrotoxicity caused by cyclosporin adminstration, said method comprising administering to a mammalian organism in need of such treatment, an effective amount to reduce nephrotoxicity caused by cyclosporin administration of an organogermanium compound represented by the formula (I)

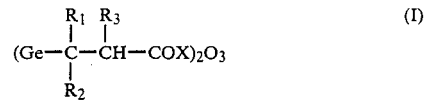

wherein $R_1$ to $R_3$ are each a hydrogen atom or a lower alkyl group which may be the same or different, or a phenyl group, and X is a hydroxyl group, a lower alkoxy group, an —$NH_2$ group of $O^-Y^+$ where Y is selected from the group consisting of a metal, lysozyme and a basic amino acid.

2. The method according to claim 1, wherein $R_1$, $R_2$ and $R_3$ are a hydrogen atom and X is a hydroxyl group.

3. The method according to claim 1 wherein said lower alkyl group is methyl, ethyl, propyl or butyl.

4. The method according to claim 1, wherein Y is a metal and said metal is sodium, potassium or Y is a lysozyme or a basic amino acid.

5. The method according to claim 4, wherein said Y is lysozyme or a basic amino acid.

6. The method according to claim 5, wherein said basic amino acid is lysine.

* * * * *